(12) United States Patent
Akagane

(10) Patent No.: US 9,199,098 B2
(45) Date of Patent: Dec. 1, 2015

(54) ULTRASONIC TREATMENT DEVICE

(71) Applicant: Olympus Corporation, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 262 days.

(21) Appl. No.: 13/942,010

(22) Filed: Jul. 15, 2013

(65) Prior Publication Data

US 2014/0066818 A1  Mar. 6, 2014

Related U.S. Application Data

(60) Provisional application No. 61/697,067, filed on Sep. 5, 2012.

(51) Int. Cl.
| | |
|---|---|
| *A61B 8/00* | (2006.01) |
| *A61N 7/00* | (2006.01) |
| *A61B 17/32* | (2006.01) |
| *A61B 17/00* | (2006.01) |

(52) U.S. Cl.
CPC .......... *A61N 7/00* (2013.01); *A61B 17/320068* (2013.01); *A61B 2017/00119* (2013.01); *A61B 2017/00473* (2013.01); *A61B 2017/00477* (2013.01)

(58) Field of Classification Search
CPC .......... A61B 8/00; A61B 8/0841; A61B 8/12; A61B 8/445; A61B 17/0057; A61B 8/0833
See application file for complete search history.

(56) References Cited

U.S. PATENT DOCUMENTS

2007/0239000 A1* 10/2007 Emery et al. .................. 600/437
2012/0078139 A1*  3/2012 Aldridge et al. ................. 601/2

FOREIGN PATENT DOCUMENTS

| JP | A-2000-175934 | 6/2000 |
| JP | A-2005-066316 | 3/2005 |

* cited by examiner

*Primary Examiner* — Joel Lamprecht
(74) *Attorney, Agent, or Firm* — Oliff PLC

(57) ABSTRACT

An ultrasonic treatment device includes a transmitting connection section connecting a proximal-side vibration transmitting section to a distal-side vibration transmitting section at an anti-node position of an ultrasonic vibration. The ultrasonic treatment device includes a detecting section detecting a coupled state in which a treatment unit is coupled with a vibrator unit or a non-coupled state in which the treatment unit is not coupled with the vibrator unit, and a supply control section controlling a supply state of a generating electric power from an electric power supply section based on a detection result of the detecting section when a first vibration generating operation is input.

7 Claims, 5 Drawing Sheets

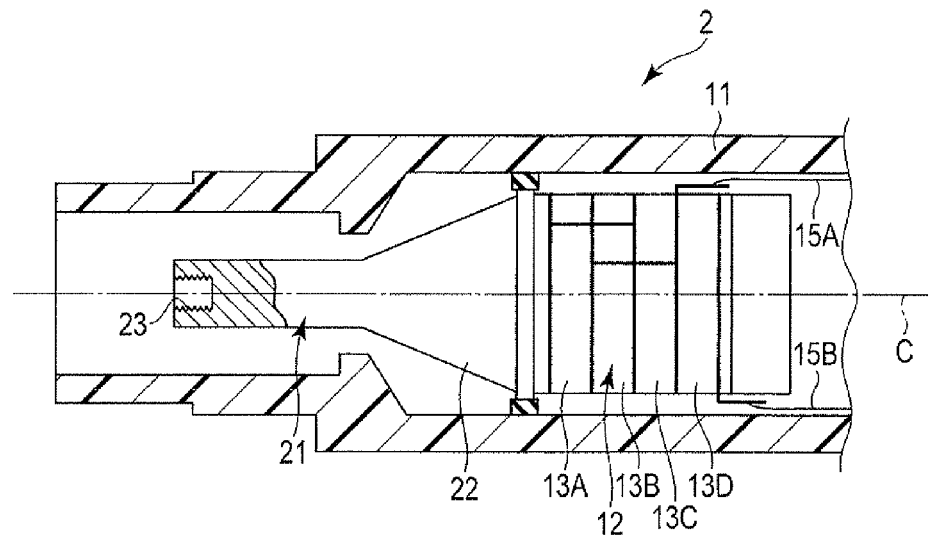
F I G. 2
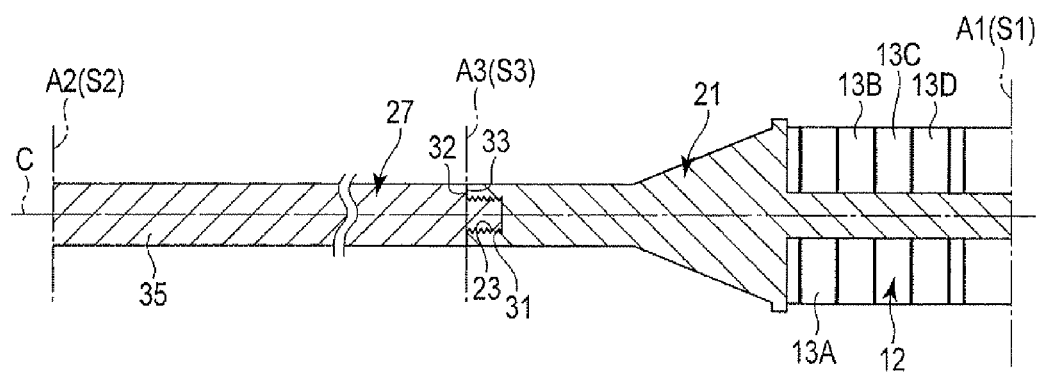
F I G. 3

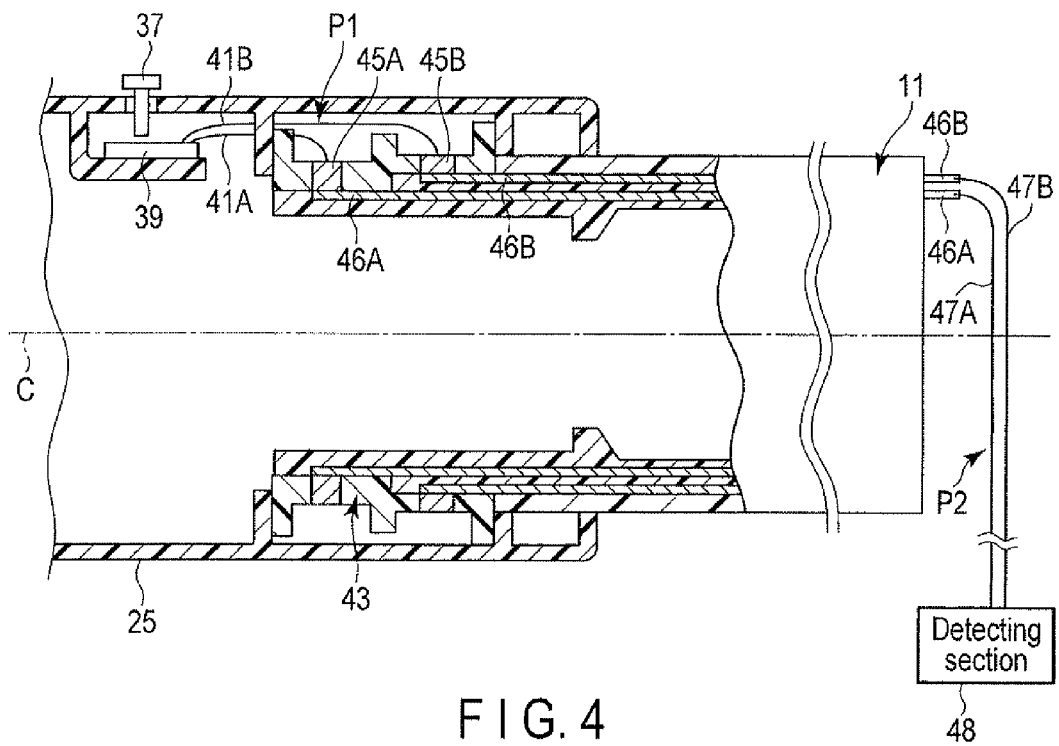
F I G. 4
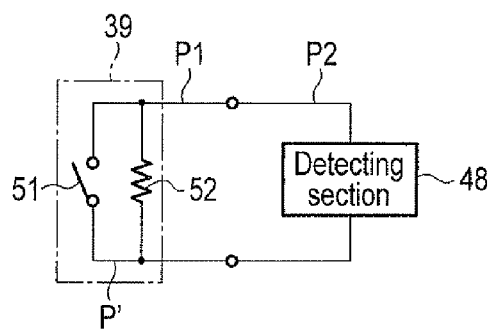
F I G. 5
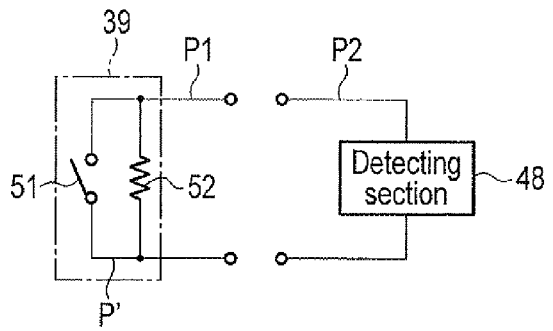
F I G. 6

ULTRASONIC TREATMENT DEVICE

CROSS-REFERENCE TO RELATED APPLICATIONS

This application claims the benefit of U.S. Provisional Application No. 61/697,067, filed Sep. 5, 2012, the entire contents of which are incorporated herein by reference.

BACKGROUND OF THE INVENTION

1. Field of the Invention

The present invention relates to an ultrasonic treatment device which treats a treatment target such as a biological tissue (body tissue) by using ultrasonic vibration.

2. Description of the Related Art

Jpn. Pat. Appln. KOKAI Publication No. 2000-175934 discloses an ultrasonic treatment device (ultrasonic surgical device). This ultrasonic treatment device includes a vibrator unit, and a treatment unit (surgery unit) which is coupled with the vibrator unit. The vibrator unit includes an ultrasonic vibrator (ultrasonic oscillator) which is a vibration generating section, and a block portion as a proximal-side vibration transmitting section to which the ultrasonic vibrator is attached and to which ultrasonic vibration is transmitted from the ultrasonic vibrator. Further, the treatment unit includes a treatment section as a distal-side vibration transmitting section which is connected to a distal direction side of the block portion and to which ultrasonic vibration is transmitted from the block section. When the ultrasonic vibration is transmitted, the block portion and the treatment section vibrate at a frequency within a predetermined frequency range. The block portion ins connected to the treatment section at an anti-node position of the ultrasonic vibration of vibrating within the predetermined frequency range.

Jpn. Pat. Appln. KOKAI Publication No. 2005-66316 also discloses an ultrasonic treatment device including a vibrator unit and a treatment unit. In this ultrasonic treatment device, the vibrator unit includes an ultrasonic vibrator which is a vibration generating section, and a fastening section as a proximal-side vibration transmitting section to which the ultrasonic vibrator is attached and to which the ultrasonic vibration from the ultrasonic vibrator is transmitted. Furthermore, the treatment unit includes a probe as a distal-side vibration transmitting section which is connected to the distal direction side of the fastening section, and to which the ultrasonic vibration from the fastening section is transmitted. The fastening section and the probe are connected via a connecting portion. When the ultrasonic vibration is transmitted, the fastening section and the probe vibrate at a frequency within a predetermined frequency range. The connecting portion is placed at a midway position different from an anti-node position of the ultrasonic vibration of vibrating within the predetermined frequency range.

BRIEF SUMMARY OF THE INVENTION

According to one aspect of the invention, an ultrasonic treatment device includes that a vibrator unit including a vibration generating section which is configured to generate ultrasonic vibration when generating electric power is supplied thereto, and a proximal-side vibration transmitting section to which the vibration generating section is attached and to which the ultrasonic vibration generated in the vibration generating section is configured to be transmitted; a treatment unit which is detachably coupled with the vibrator unit, the treatment unit including a distal-side vibration transmitting section which is connected to a distal direction side of the proximal-side vibration transmitting section in a coupled state in which the treatment unit is coupled with the vibrator unit, and to which the ultrasonic vibration is configured to be transmitted from the proximal-side vibration transmitting section in the coupled state; a first operation input section which is provided separately from the treatment unit, and which is configured to input a first vibration generating operation of generating the ultrasonic vibration in the vibration generating section; an electric power supply section which is configured to supply the generating electric power to the vibration generating section in the coupled state so that the proximal-side vibration transmitting section and the distal-side vibration transmitting section vibrate at a reference frequency, the reference frequency being a frequency at which an impedance of the generating electric power takes minimum value within a predetermined frequency range; a transmitting connection section which connects the proximal-side vibration transmitting section to the distal-side vibration transmitting section at an anti-node position of the ultrasonic vibration at the reference frequency in the coupled state; a detecting section which is configured to detect the coupled state in which the treatment unit is coupled with the vibrator unit or a non-coupled state in which the treatment unit is not coupled with the vibrator unit; and a supply control section which is configured to control a supply state of the generating electric power from the electric power supply section based on a detection result of the detecting section when the first vibration generating operation is input, the supply control section being configured to control the supply state so that the generating electric power is supplied to the vibration generating section when the coupled state has been detected and so that the generating electric power is not supplied to the vibration generating section when the non-coupled state has been detected.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a cross-sectional view schematically showing a configuration of a vibrator unit according to the first embodiment;

FIG. 3 is a cross-sectional view schematically showing a configuration of an ultrasonic vibrator, a vibration transmitting member, and a probe according to the first embodiment;

FIG. 4 is a schematic view showing an electrical connecting state between an operation button and a control unit according to the first embodiment;

FIG. 5 is a circuit diagram showing an electrical path between a detecting section and an electronic circuit board when a treatment unit and a vibrator unit are coupled with each other according to the first embodiment;

FIG. 6 is a circuit diagram showing an electrical path between the detecting section and the electronic circuit board when the treatment unit and the vibrator unit are not coupled with each other according to the first embodiment;

DETAILED DESCRIPTION OF THE INVENTION

First Embodiment

Figure 1:
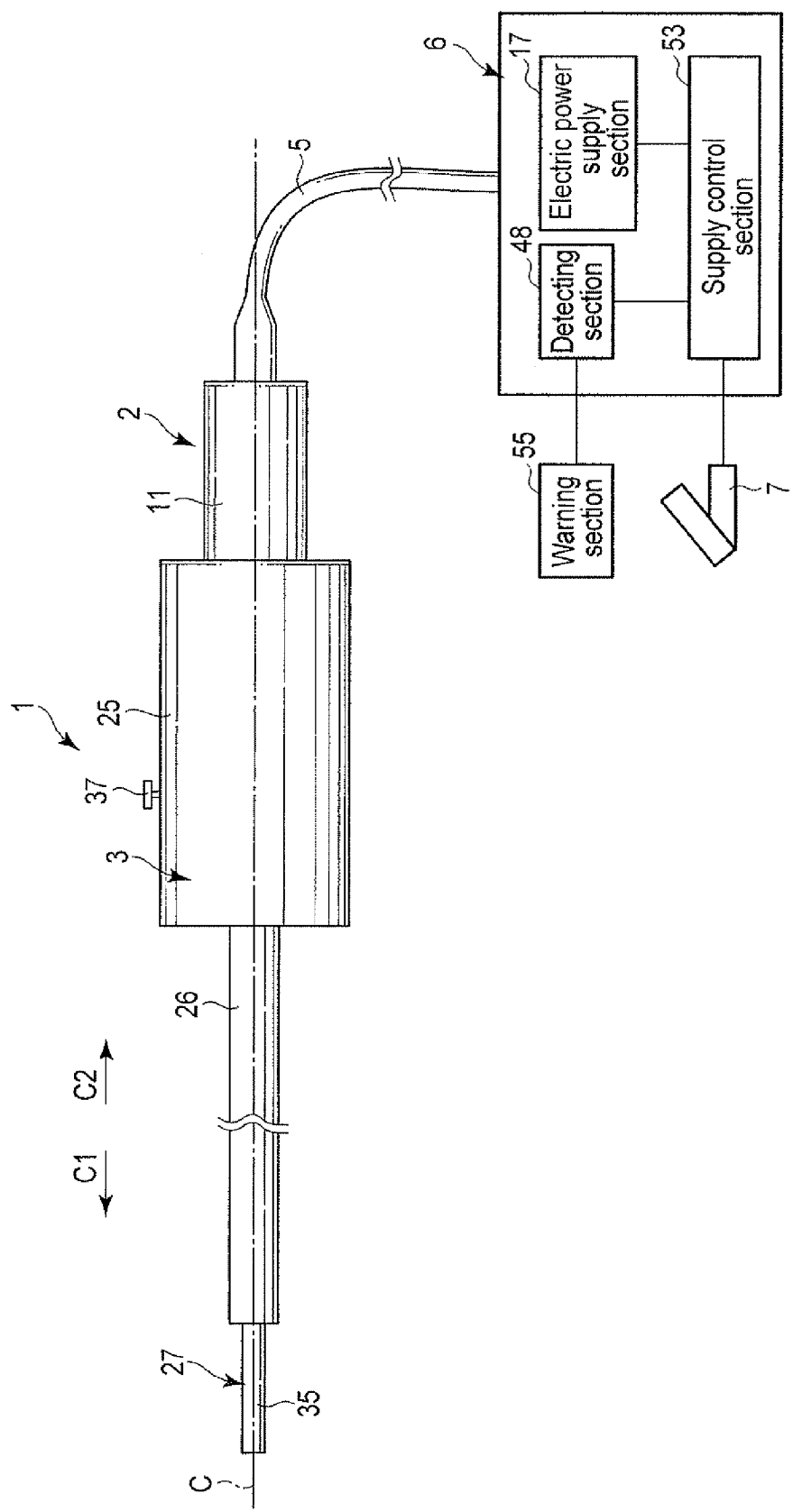
FIG. 1 is a schematic view showing an ultrasonic treatment device according to a first embodiment of the present invention.

A first embodiment according to the present invention will now be described with reference to FIG. 1 to FIG. 9. FIG. 1 is a view showing an ultrasonic treatment device (ultrasonic surgical device) 1 according to this embodiment. As shown in FIG. 1, the ultrasonic treatment device 1 has a longitudinal axis C. Here, it is assumed that one of two directions parallel to the longitudinal axis C is a distal direction (a direction of an arrow C1 in FIG. 1), and a direction opposite to the distal direction is a proximal direction (a direction of an arrow C2 in FIG. 1). The ultrasonic treatment device 1 includes a vibrator unit (oscillator unit) 2 and a treatment unit (surgery unit) 3 detachably coupled with the vibrator unit 2. The treatment unit 3 is coupled with the vibrator unit 2 from the distal direction side. One end of a cable 5 is connected to a proximal end of the vibrator unit 2. The other end of the cable 5 is connected to a control unit 6. The control unit 6 is electrically connected to a foot switch 7 which is a first operation input section. The foot switch 7 is provided separately from the vibrator unit 2 and the treatment unit 3.

FIG. 2 is a view showing a configuration of the vibrator unit 2. As shown in FIG. 2, the vibrator unit 2 includes a vibrator case (oscillator case) 11. One end of the cable 5 is connected to the vibrator case 11. An ultrasonic vibrator (ultrasonic oscillator) 12 as a vibration generating section is provided in the vibrator case 11. The ultrasonic vibrator 12 includes piezoelectric elements 13A to 13D configured to convert generating electric power (electric power) into ultrasonic vibration. One end of each of electrical wiring lines 15A and 15B is connected to the ultrasonic vibrator 12.

As shown in FIG. 1, the control unit 6 includes an electric power supply section 17. The other end of each of the electrical wiring lines 15A and 15B is connected to the electric power supply section 17 through an inside of the cable 5. When the generating electric power is supplied to the ultrasonic vibrator 12 from the electric power supply section 17 through the electrical wiring lines 15A and 15B, the ultrasonic vibrator 12 generates ultrasonic vibration. Moreover, a first vibration generating operation of generating the ultrasonic vibration in the ultrasonic vibrator 12 is input in the foot switch 7.

As shown in FIG. 2, the vibrator unit 2 includes a vibration transmitting member 21 as a proximal-side vibration transmitting section to which the ultrasonic vibrator 12 is attached. The vibration transmitting member 21 is extended along the longitudinal axis C, and the ultrasonic vibration generated by the ultrasonic vibrator 12 is transmitted thereto. In the vibration transmitting member 21, the ultrasonic vibration is transmitted from the proximal direction to the distal direction. A horn section 22 is provided to the vibration transmitting member 21, the horn section 22 is located to the distal direction side of the ultrasonic vibrator 12. The horn section 22 is configured to increase amplitude of the ultrasonic vibration. Additionally, a female screw portion 23 is provided to a distal end portion of the vibration transmitting member 21.

As shown in FIG. 1, the treatment unit 3 includes a holding case 25, and a sheath 26 extended from an inside of the holding case 25 toward the distal direction. The sheath 26 is inserted into the holding case 25 from the distal direction side. Further, a probe 27 as a distal-side vibration transmitting section is extended along the longitudinal axis C in (inside) the sheath 26. The probe 27 is extended to a part located to a distal direction side of a distal end of the sheath 26. In case of coupling the treatment unit 3 with the vibrator unit 2, the vibrator unit 2 is inserted into the holding case 25 from the proximal direction side. Furthermore, in a coupled state in which the vibrator unit 2 is coupled with the treatment unit 3, the probe 27 is connected to the vibration transmitting member 21 in (inside) the sheath 26 and the vibrator case 11.

FIG. 3 is a view showing a configuration of the ultrasonic vibrator 12, the vibration transmitting member 21, and the probe 27 in the form of a cross section running through the longitudinal axis C. As shown in FIG. 3, a male screw portion 31 is provided to a proximal end portion of the probe 27. When the male screw section 31 is screwed to the female screw portion 23 of the vibration transmitting member 21, the probe 27 as the distal-side vibration transmitting section is connected to the distal direction side of the vibration transmitting member 21 that is the proximal-side vibration transmitting section. A proximal-side abutting portion 32 is provided to the vibration transmitting member 21, and a distal-side abutting portion 33 is provided to the probe 27. The proximal-side abutting portion 32 is a distal end of the vibration transmitting member 21. When the probe 27 is connected to the vibration transmitting member 21, the proximal-side abutting portion 32 abuts on the distal-side abutting portion 33. As a result, the ultrasonic vibration can be transmitted from the vibration transmitting member 21 to the probe 27 through the proximal-side abutting portion 32 and the distal-side abutting portion 33. That is, the vibration transmitting member 21 is connected to the probe 27 by the proximal-side abutting portion 32 and the distal-side abutting portion 33 which are transmitting connection sections.

A treatment section (surgery section) 35 is provided to a distal end portion of the probe 27. In the probe 27, the ultrasonic vibration is transmitted from the proximal direction to the distal direction. In the treatment section 35, a treatment (surgery) is given to a treatment target (surgery target) such as a biological tissue (body tissue) by using the ultrasonic vibration. Here, the ultrasonic vibration is longitudinal vibration whose vibrating directions and transmitting direction are parallel to the longitudinal axis C.

As shown in FIG. 1, an operation button 37 as a second operation input section is attached to the holding case 25. The operation button 37 is configured to input a second vibration generating operation of generating the ultrasonic vibration in the ultrasonic vibrator 12.

FIG. 4 is a view showing an electrical connecting state between the operation button 37 and the control unit 6. It is to be noted that FIG. 4 shows a coupled state in which the vibrator unit 2 is coupled with the treatment unit 3. As shown in FIG. 4, the treatment unit 3 includes an electronic circuit board 39 provided in the holding case 25. One end of each of electrical wiring lines 41A and 41B is connected to the electronic circuit board 39. Furthermore, the treatment unit 3 includes a connection ring 43 fixed to the holding case 25. Electrical relay sections 45A and 45B having conductive properties are provided to the connection ring 43. Electrical relay sections 45A and 45B are electrically insulated from each other. The other end of electrical wiring line 41A is connected to electrical relay section 45A. The other end of electrical wiring line 41B is connected to electrical relay section 45B.

Conductive sections 46A and 46B are provided to (in) the vibrator case 11. Conductive sections 46A and 46B are electrically insulated from each other. In the coupled state in which the vibrator unit 2 is coupled with the treatment unit 3, conductive section 46A abuts on electrical relay section 45A and is electrically connected to electrical relay section 45A. Additionally, in the coupled state in which the vibrator unit 2 is coupled with the treatment unit 3, conductive section 46B abuts on electrical relay section 45B and is electrically connected to electrical relay section 45B. Here, in a non-coupled state in which the treatment unit 3 is not coupled with the vibrator unit 2, conductive section 46A is not in contact with the electrical relay section 45, and it is electrically disconnected from electrical relay section 45A. Further, in the non-coupled state, conductive section 46B is not in contact with electrical relay section 45B, and it is electrically disconnected from electrical relay section 45B.

One end of an electrical wiring line 47A is connected to conductive section 46A. Furthermore, one end of an electrical wiring line 47B is connected to conductive section 46B. A detecting section 48 is provided to the control unit 6. Electrical wiring lines 47A and 47B are extended through the inside of the cable 5. The other end of the cable 5 is connected to the detecting section 48.

Each of FIG. 5 and FIG. 6 is a view showing an electrical path between the detecting section 48 and the electronic circuit board 39. Here, FIG. 5 shows the coupled state in which the vibrator unit 2 is coupled with the treatment unit 3, and FIG. 6 shows the non-coupled state in which the vibrator unit 2 is not coupled with the treatment unit 3. As shown in FIG. 5 and FIG. 6, a switch section 51 is provided to the electronic circuit board 39. When the second vibration generating operation is input by the operation button 37, the switch section 51 is closed. When the second vibration generating operation is not input, the switch section 51 is opened. The switch section 51 is electrically connected to electrical wiring lines 41A and 41B through an electronic circuit (not shown) provided on the electronic circuit board 39. It is to be noted that, in FIG. 5 and FIG. 6, the switch section 51 is opened.

Moreover, a resistor 52 as an electronic element is provided to the electronic circuit board 39. The resistor 52 is electrically connected to electrical wiring lines 41A and 41B through an electronic circuit (not shown) provided to the electronic circuit board 39. That is, the electronic circuit provided to the electronic circuit board 39, electrical wiring lines 41A and 41B, and electrical relay sections 45A and 45B form a distal-side electrical path section P1 which is electrically connected to the resistor 52 as the electronic element. The distal-side electrical path section P1 is provided to (in) the treatment unit 3. The resistor 52 is connected to the switch section 51 with the resistor 52 being electrically parallel with respect to the switch section 51. The resistor 52 is connected to the switch section 51 through the distal-side electrical path section P1 (an electronic circuit provided on the electronic circuit board 39).

Additionally, conductive sections 46A and 46B and electrical wiring lines 47A and 47B form a proximal-side electrical path section P2. The proximal-side electrical path section P2 is extended through the vibrator unit 2 and the inside of the cable 5. In the coupled state in which the vibrator unit 2 is coupled with the treatment unit 3, conductive section 46A is electrically connected to electrical relay section 45A, and conductive section 46B is electrically connected to electrical relay section 45B. Therefore, in the coupled state, the proximal-side electrical path section P2 is electrically connected to the distal-side electrical path section P1. Therefore, in the coupled state, the switch section 51 and the resistor 52 are electrically connected to the detecting section 48 through the distal-side electrical path section P1 and the proximal-side electrical path section P2.

On the other hand, in the non-coupled state in which the vibrator unit 2 is not coupled with the treatment unit 3, conductive section 46A is electrically disconnected from electrical relay section 45A, and conductive section 46B is electrically disconnected from electrical relay section 45B. Therefore, in the non-coupled state, the proximal-side electrical path section P2 is electrically disconnected from the distal-side electrical path section P1. Accordingly, in the non-coupled state, the switch section 51 and the resistor 52 are electrically disconnected from the detecting section 48.

The detecting section 48 is configured to supply (output) detection electric power at fixed time intervals through the proximal-side electrical path section P2. Further, whether the treatment unit 3 and the vibrator unit 2 are the coupled state or the non-coupled state is detected based on a resistance R which is one of electrical characteristic values of the detection electric power. Furthermore, in the coupled state, the detecting section 48 detects an opened or closed state of the switch section 51 based on the resistance R of the detection electric power.

As shown in FIG. 1, the control unit 6 includes a supply control section 53 configured to control a supply state of generating electric power from the electric power supply section 17 to the ultrasonic vibrator 12. The supply control section 53 is electrically connected to the foot switch 7, the electric power supply section 17, and the detecting section 48. The supply control section 53 is configured to control a supply state of the generating electric power from the electric power supply section 17 based on input of the first vibration generating operation using the foot switch 7 and a detection result obtained by the detecting section 48. Moreover, the detecting section 48 is electrically connected to a warning section 55. The warning section 55 is configured to warn an error state when the detecting section 48 has detected the non-coupled state of the treatment unit 3 and the vibrator unit 2. The warning section 55 is, e.g., a display, a light, or a buzzer.

In the coupled state, when the ultrasonic vibration is generated by supply of the generating electric power, the vibration transmitting member (the proximal-side vibration transmitting section) 21 and the probe (the distal-side vibration transmitting section) 27 vibrate at later-described reference frequency (f1; f2). As shown in FIG. 3, in the ultrasonic vibration at the reference frequency (f1; f2), a proximal end of the vibration transmitting member 21 is located at an anti-node position A1, and a distal end of the probe 27 is located at an anti-node position A2. Additionally, in the ultrasonic vibration at the reference frequency (f1; f2), the vibration transmitting member 21 and the probe 27 are connected at an anti-node position A3 different from anti-node positions A1 and A2. Therefore, the proximal-side abutting portion 32 and the distal-side abutting portion 33 are placed at anti-node position A3 of the ultrasonic vibration at the reference frequency (f1; f2).

Functions and effects of the ultrasonic treatment device 1 according to this embodiment will now be described. In the ultrasonic treatment device 1, the detection electric power is supplied from the detecting section 48 through the proximal-side electrical path section P2. The detecting section 48 detects the coupled state or the non-coupled state between the treatment unit 3 and the vibrator unit 2 based on the resistance R which is one of electrical characteristic values of the detection electric power. Further, in the coupled state, the detection unit 48 detects whether the switch section 51 is the opened state or the closed state based on the resistance R of the detection electric power.

Figure 7:
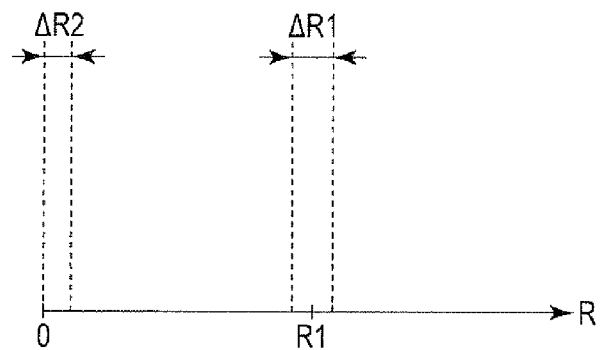
FIG. 7 is a schematic view explaining detection in the detecting section according to the first embodiment.

FIG. 7 is a view for explaining detection in the detecting section 48. In the non-coupled state in which the treatment unit 3 is not coupled with the vibrator unit 2, as shown in FIG. 6, the distal-side electrical path section P1 is electrically disconnected from the proximal-side electrical path section P2. Therefore, the detection electric power is not supplied to the distal-side electrical path section P1, and the detection electric power is not supplied to the switch section 51 and the resistor 52. Therefore, in the non-coupled state, the resistance R of the detection electric power is infinite ($\infty$).

In the coupled state in which the treatment unit 3 is coupled with the vibrator unit 2, as shown in FIG. 5, the distal-side electrical path section P1 is electrically connected to the proximal-side electrical path section 22. Therefore, in the coupled state, the detection electric power is supplied to the distal-side electrical path section P1. In the coupled state, when the second vibration generating operation is not input by using the operation button 37, the switch section 51 is opened. In this case, a detection electric current which is a current of the detection electric power does not pass through the switch section 51 but passes through the resistor 52. Here, if the resistor 52 has a resistance R1, the resistance R of the detection electric power is R1.

On the other hand, in the coupled state, when the second vibration generating operation is input by using the operation button 37, the switch section 51 is closed. In this case, the detection electric current of the detection electric power does not pass through the resistor 52 but passes through the switch section 51. Therefore, the resistance R of the detection electric power is zero.

As shown in FIG. 7, in the resistance R of the detection electric power, a region near R1 including R1 is determined as a first resistance region (a first characteristic value region) $\Delta R1$. Furthermore, in the resistance R of the detection electric power, a region near zero including zero is determined as a second resistance region (a second characteristic value region) $\Delta R2$. The first resistance region $\Delta R1$ and the second resistance region $\Delta R2$ are regions different from each other. When the resistance (the electrical characteristic value) R of the detection electric power is in the first resistance region $\Delta R1$ or the second resistance region $\Delta R2$, the detecting section 48 detects that the treatment unit 3 is coupled with the vibrator unit 2. On the other hand, when the resistance R of the detection electric power is not in the first resistance region $\Delta R1$ and the second resistance region $\Delta R2$ either, the detecting section 48 detects that the treatment unit 3 is not coupled with the vibrator unit 2.

Moreover, when the resistance R of the detection electric power is in the first resistance region $\Delta R1$, the detecting section 48 detects that the switch section 51 is opened. On the other hand, when the resistance of the detection electric power is in the second resistance region $\Delta R2$, the detecting section detects that the switch section 51 is closed.

When the first vibration generating operation is input by using the foot switch 7, the supply control section 53 controls the supply state of the generating electric current from the electric power supply section 17 based on a detection result indicating the coupled state or the non-coupled state obtained by the detecting section 48. That is, when the detecting section 48 has detected the coupled state (when the resistance R is in the first resistance region $\Delta R1$), the supply control section 53 controls the supply state so that the generating electric power is supplied to the ultrasonic vibrator 12. On the other hand, when the detecting section 48 has detected the non-coupled state (the resistance R is not in the first resistance region $\Delta R1$), the supply control section 53 controls the supply state so that the generating electric power is not supplied to the ultrasonic vibrator 12. Even if the first vibration generating operation is input, in the non-coupled state, the generated electric power is not supplied to the ultrasonic vibrator 12. Therefore, in the non-coupled state, the ultrasonic vibration is not generated by the ultrasonic vibrator 12.

Additionally, when the detecting section 48 has detected the closed state of the switch 51, the supply control section 53 controls the electric power supply section 17 so that the generating electric power is supplied to the ultrasonic vibrator 12. Therefore, when the closed state of the switch section 51 has been detected, the ultrasonic vibration is generated by the ultrasonic vibrator 12.

Figure 8:
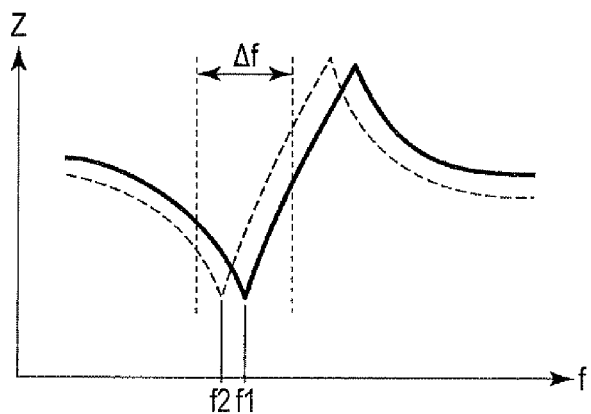
FIG. 8 is a schematic view showing a relationship between a frequency of ultrasonic vibration and impedance of generating electric power when a vibration transmitting member and a probe are coupled with each other according to the first embodiment.

FIG. 8 is a view showing a relationship between a frequency f of the ultrasonic vibration of the vibration transmitting member (the proximal-side vibration transmitting section) 21 and the probe (the distal-side vibration transmitting section) 27 in the coupled state and impedance Z of the generating electric power. As shown in FIG. 8, when the generating electric power is supplied from the electric power supply section 17, the vibration transmitting member 21 and the probe 27 in the coupled state vibrate at a reference frequency (f1; f2) that is within a predetermined frequency range $\Delta f$.

Here, in manufacture of the ultrasonic treatment device 1, a material composition ratio, a dimension, and others slightly differ in accordance with each vibration transmitting member 21. Likewise, a material composition ratio, a dimension, and others slightly differ in accordance with each probe 27. Therefore, the reference frequency (f1; f2), which is a frequency at the time of vibrating the vibration transmitting member 21 and the probe 27 in the coupled state, differ in accordance with each ultrasonic treatment device 1 due to characteristics of the vibrating transmitting member 21, characteristic of the probe 27, a combination of the vibration transmitting member 21 and the probe 27, and others.

Here, the reference frequency (f1; f2) is a frequency at which the impedance Z of the generating electric power takes a minimum vale in the predetermined frequency range (predetermined frequency domain) $\Delta f$. For example, in one ultrasonic treatment device 1, as indicated by a solid line in FIG. 8, the generating electric power is supplied to the ultrasonic vibrator 12 so that the probe 27 and the vibration transmitting member 21 in the coupled state vibrate at the reference frequency f1. In one another ultrasonic treatment device 1, as indicted by a dotted line in FIG. 8, the generating electric power is supplied to the ultrasonic vibrator 12 so that the probe 27 and the vibration transmitting member 21 in the coupled state vibrate at the reference frequency f2. That is, like phase lock loop (PLL) control, the reference frequency (f1; f2) of the probe 27 and the vibration transmitting member 21 in the coupled state and the generating electric power are controlled.

Figure 9:
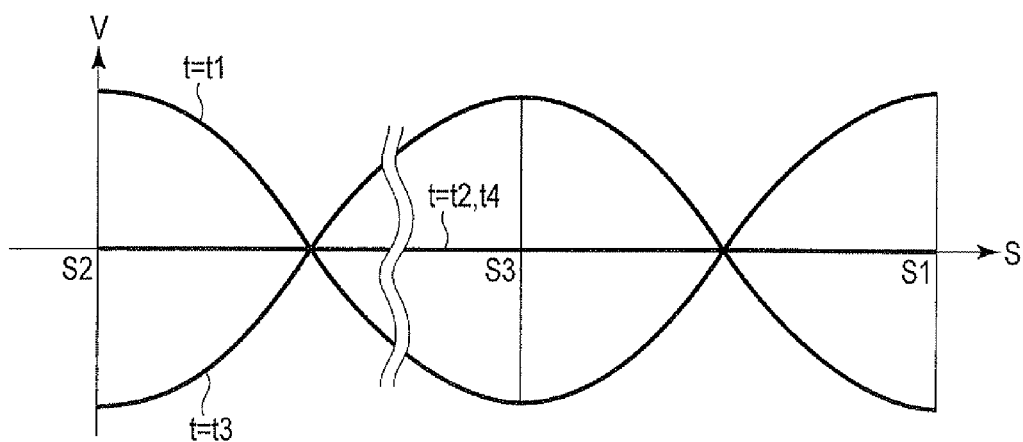
FIG. 9 is a schematic view showing a change in ultrasonic vibration at a reference frequency relative to a change in position along a longitudinal axis when the probe and the vibration transmitting member are coupled with each other according to the first embodiment.

FIG. 9 is a view showing a change in ultrasonic vibration (v) at the reference frequency (f1; f2) relative to a change in position S along the longitudinal axis C when the probe 27 and the vibration transmitting member 21 are in the coupled state. It is to be noted that FIG. 9 shows the ultrasonic vibration (v) at a time t=t1, t2, t3, or t4. As shown in FIG. 3 and FIG. 9, in the ultrasonic vibration at the reference frequency (f1; f2), a position S1 corresponding to a proximal end of the vibration transmitting member 21 is an anti-node position A1. Furthermore, a position S2 corresponding to a distal end of the probe 27 is an anti-node position A2. Moreover, a position S3 corresponding to a distal end of the vibration transmitting member 21 is an anti-node position A3 different from anti-node positions A1 and A2. In the coupled state, the proximal-side abutting portion 32 of the vibration transmitting member 21 and the distal-side abutting portion 33 of the probe 27 are placed at the position S3. That is, in the coupled state, the proximal-side abutting portion 32 and the distal-side abutting portion 33 are placed at anti-node position A3 of the ultrasonic vibration at the reference frequency (f1; f2).

The proximal-side abutting portion 32 and the distal-side abutting portion 33, in which the ultrasonic vibration is transmitted from the vibration transmitting member (the proximal-side vibration transmitting section) 21 to the probe (the distal-side vibration transmitting section) 27, abut on (are joined to) each other at anti-node position A3 of the ultrasonic vibration. At the anti-node positions (A1 to A3) of the ultrasonic vibration including anti-node position A3, although an amplitude becomes maximum, stress in directions parallel to the longitudinal axis is zero. Therefore, when the proximal-side abutting portion 32 and the distal-side abutting portion 33 are provided at anti-node position A3, stress does not act on the connecting portion of the vibration transmitting member 21 and the probe 27. As a result, loss of the vibration energy at the proximal-side abutting portion 32 and the distal-side abutting portion 33 can be effectively avoided. Therefore, the loss of the ultrasonic vibration in the treatment section 35 is reduced, a treatment can be efficiently given by the treatment section 35 using the ultrasonic vibration.

Here, since the proximal-side abutting portion 32 is provided at anti-node position A3 of the ultrasonic vibration at the reference frequency (f1; f2), the distal end of the vibration transmitting member (the proximal-side vibration transmitting section) 21 is at anti-node position A3. Therefore, when the generating electric power is supplied to the ultrasonic vibrator 12 and the ultrasonic vibration is generated, the vibration transmitting member 21 solely vibrates within the predetermined frequency range Δf even in the non-coupled state. Therefore, whether it is in the coupled state or the non-coupled state cannot be identified from frequency characteristic of the vibration of the vibration transmitting member 21.

Thus, in this embodiment, when the detecting section 48 has detected that the treatment unit 3 is not coupled with the vibrator unit 2, the electric power supply section 17 is controlled so that the generating electric power is not supplied to the ultrasonic vibrator 12. Therefore, in the non-coupled state, the ultrasonic vibration is not generated in the ultrasonic vibrator 12, and the vibration of the vibration transmitting member 21 in the non-coupled state can be effectively avoided. That is, in the non-coupled state, since the generating electric power is not supplied to the ultrasonic vibrator 12, even when the distal end and the proximal end of the vibrating transmitting member 21 are provided at the anti-node positions (A2, A3), the vibration transmitting member 21 does not vibrate. When the vibration of the vibration transmitting member 21 in the non-coupled state is avoided, safety in a treatment can be assured.

Additionally, in the coupled state, the switch section 51 and the resistor 52, which is an electronic element, are electrically connected to the detecting section 48 via the common proximal-side electrical circuit path section P2. Further, in the distal-side electrical path section P1, likewise, an electrical path between the switch section 51 and the proximal-side electrical path section P2 and an electrical path between the resistor 52 and the proximal-side electrical path section P2 have a commonality except an electronic circuit (not shown) of the electronic circuit board 39. That is, in the proximal-side electrical path section P2 and the distal-side electrical path section P1 in the coupled state, a large part of a switch line P' between the switch section 51 and the detecting section 48 and an electrical path between the resistor 52 and the detecting section 48 have a commonality. Therefore, the resistor 52 of the treatment unit 3 can be electrically connected to the detecting section 48 by using the switch line P'. Therefore, even when the resistor 52 as the electronic element is provided in the treatment unit 3, the configuration of the ultrasonic treatment device 1 is not complicated.

Modification

Figure 10:
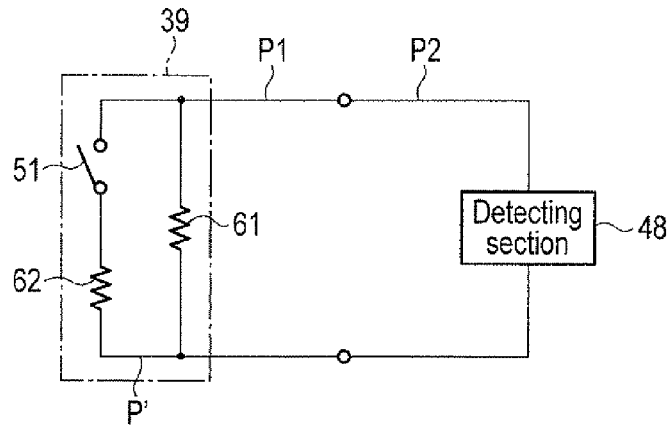
FIG. 10 is a circuit diagram showing an electrical path between a detecting section and an electronic circuit board according to a first modification.
Figure 11:
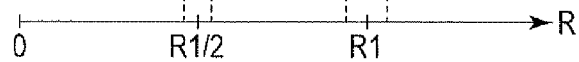
FIG. 11 is a schematic view explaining detection in the detecting section according to the first modification.

It is to be noted that, in the first embodiment, the resistor 52 is provided as the electronic element and the resistor 52 is electrically parallel with respect to the switch section 51, but the present invention is not restricted thereto. For example, as a first modification, two resistors 61 and 62 may be provided as electronic elements to the electronic circuit board 39 as shown in FIG. 10 and FIG. 11. The resistor 61 is electrically parallel with respect to the switch section 51. Further, the resistor 62 is electrically in series with respect to the switch section 51 and electrically parallel with respect to the resistor 61. The resistor 61, the resistor 62, and the switch section 51 are electrically connected to each other through the dista-side electrical path section P1.

In this modification, like the first embodiment, the resistance R of the detection electric power is infinite (∞) in the non-coupled state. Furthermore, in the coupled state, the detection electric power is supplied to the distal-side electrical path section P1. In the coupled state, when the switch section 51 is opened, the detection electric current of the detection electric power passes through the resistor 61 without passing through the switch section 51 and the resistor 62. Here, if each of the resistors 61 and 62 has a resistance R1, the resistance R of the detection electric power is R1. On the other hand, in the coupled state, when the switch section 51 is closed, the detection electric current of the detection electric power passes through the switch section 51 and the resistor 62 and also passes through the resistor 61. In this case, the resistance R of the detection electric power is R1/2.

In this modification, according to the resistance R of the detection electric power, a region near R1 including R1 is a first resistance region (a first characteristic value region) ΔR1, and a region near R1/2 including R1/2 is a second resistance region (a second characteristic value region) ΔR2. When the resistance (the electrical characteristic value) R of the detection electric power is in the first resistance region ΔR1 or the second resistance region ΔR2, the detecting section 48 detects that the treatment unit 3 is coupled with the vibrator unit 2. On the other hand, when the resistance R of the detection electric power is not in the first resistance region ΔR1 and not in the second resistance region ΔR2 either, the detecting section 48 detects that the treatment unit 3 is not coupled with the vibrator unit 2.

Figure 12:
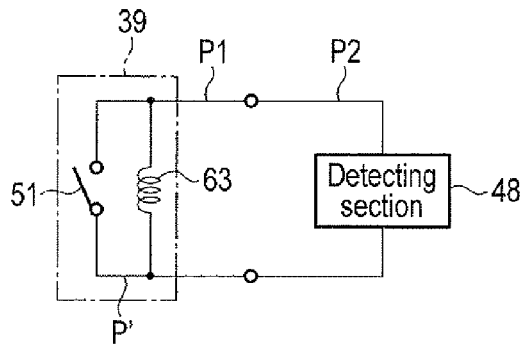
FIG. 12 is a circuit diagram showing an electrical path between the detecting section and the electronic circuit board according to a second modification.

Furthermore, as a second modification, a coil 63 may be provided as an electronic element as shown in FIG. 12. The coil 63 is electrically parallel with respect to the switch section 51, and electrically connected to the switch section 51 through the distal-side electrical path section P1. In this modification, based on inductance L, which is one of electrical characteristic values of the detection electric power, instead of the resistance R, the detecting section 48 detects whether the treatment unit 3 is coupled with or not coupled with the vibrator unit 2. Moreover, in the coupled state, the detecting section 48 detects an opened state or a closed state of the switch section 51 based on the inductance L of the detected electric power. That is, the inductance L of the detection electric power varies between the coupled state and the non-coupled state. Additionally, the inductance L of the detection electric power varies between the opened state and the closed state of the switch section 51.

Figure 13:
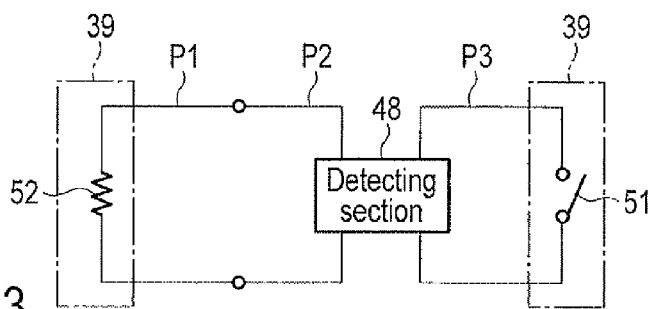
FIG. 13 is a circuit diagram showing an electrical path between a detecting section and an electronic circuit board according to a third modification.

Further, in the first embodiment, the switch section 51 is electrically connected to the detecting section 48 through the proximal-side electrical path section P2 and the distal-side electrical path section P1 in the coupled state, but the present invention is not restricted thereto. For example, as a third modification, the switch section 51 is electrically connected to the detecting section 48 through a switch line P3 different from the proximal-side electrical path section P2 and the distal-side electrical path section P1 as shown in FIG. 13.

In this modification, the detecting section 48 supplies first detection electric power (detection electric power) through the proximal-side electrical path section P2. Further, based on an electrical characteristic value such as a resistance (R) of the first detection electric power, a coupled state or a non-coupled state between the treatment unit 3 and the vibrator unit 2 is detected. Furthermore, the detecting section 48 supplies second detection electric power through the switch line P3. Moreover, based on an electrical characteristic value such as a resistance of the second detection electric power, an opened state or a closed state of the switch section 51 is detected.

It is to be noted that, as the electronic elements provided in the treatment unit 3, there are a capacitor, an IC circuit (an integrated circuit), an electrical line and others in addition to the resistor and the coil. Additionally, the first operation input section is not restricted to the foot switch 7, and it may be a manual lever, a touch panel, a voice input section, or the like. That is, providing the first operation input section separately from the treatment unit 3 can suffice.

Further, a jaw (not shown) may be pivotally attached to a distal end portion of the sheath 26 so that the jaw can be opened or closed with respect to the treatment section 35 of the probe 27. In this case, a rotary operation knob as a rotary operating section is attached to the holding case 25, and the probe 27, the sheath 26, and the jaw rotate in one of periaxial directions of the longitudinal axis with respect to the holding case 25. Furthermore, in this case, in addition to a treatment given by the treatment unit 35 using the ultrasonic vibration, a treatment using a high-frequency current may be given with use of the treatment section 35 and the jaw serving as electrodes.

Based on the foregoing modification, in the coupled state, the proximal-side vibration transmitting section (21) and the distal-side vibration transmitting section (27) may be connected to each other at the anti-node position (A3) of the ultrasonic vibration with the reference frequency (f1; f2). Moreover, the electronic element (51; 61, 62; 63) may be electrically connected to the distal-side electrical path section P1. Additionally, the proximal-side electrical path section P2 may be electrically connected to the distal-side electrical path section P1 in the coupled state, and the distal-side electrical path section P1 may be electrically disconnected from the proximal-side electrical path section P2 in the non-coupled state. Further, the detecting section 48 may supply the detection electric power through the proximal-side electric path section P2 and detect the coupled state or the non-coupled state based on each electrical characteristic value (R; L) of the detection electric power. Furthermore, the supply control section 53 may control a supply state of the electric power supply section 17 so that the generating electric power is supplied to the vibration generating section (12) when the coupled state has been detected and so that the generating electric power is not supplied to the vibration generating section (12) when the non-coupled state has been detected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasonic treatment device comprising:
an electric power output section that is configured to output a driving electric power;
a vibrator unit including an ultrasonic vibrator which is configured to generate an ultrasonic vibration when the driving electric power output from the electric power output section is supplied thereto, and a proximal-side vibration transmitting section to which the ultrasonic vibrator is attached and to which the ultrasonic vibration generated in the ultrasonic vibrator is configured to be transmitted;
a treatment unit which is detachably coupled with the vibrator unit, the treatment unit including a distal-side vibration transmitting section which is detachably connected to a distal direction side of the proximal-side vibration transmitting section at a connecting position only when the treatment unit is coupled with the vibrator unit, and to which the ultrasonic vibration is configured to be transmitted from the proximal-side vibration transmitting section when the distal-side vibration transmitting section is connected to the proximal-side vibration transmitting section at the connecting position, the proximal-side vibration transmitting section and the distal-side vibration transmitting section being configured to transmit the ultrasonic vibration so that the proximal-side vibration transmitting section and the distal-side vibration transmitting section integrally vibrate at a reference frequency, the proximal-side vibration transmitting section and the distal-side vibration transmitting section being configured to vibrate at the reference frequency so that one of anti-node positions of the ultrasonic vibration is located at the connecting position between the proximal-side vibration transmitting section and the distal-side vibration transmitting section;
an operation input section in which an operation is configured to be input;

a detecting section that is configured to detect whether or not the treatment unit is coupled with the vibrator unit; and an output control section which is configured to control an output of the driving electric power from the electric power output section based on a detection result of the detecting section and whether or not the operation is input in the operation input section, the output control section being configured to control the output of the driving electric power so that the driving electric power is output from the electric power output section only when the operation is input in the operation input portion and the detecting section detects that the treatment unit is coupled with the vibrator unit.

2. The device according to claim 1,
wherein the treatment unit includes an electronic element, and a distal-side electrical path section electrically connected to the electronic element, the vibrator unit includes a proximal-side electrical path section which is configured to be electrically connected to the distal-side electrical path section only when the treatment unit is coupled with the vibrator unit; and the detecting section is configured to output a detection electric power through the proximal-side electrical path section, and configured to detect whether or not the treatment unit is coupled with the vibrator unit based on an electrical characteristic value of the detection electric power.

3. The device according to claim 2,
wherein the detecting section is configured to detect that the treatment unit is coupled with the vibrator unit when the electrical characteristic value of the detection electric power is in a first characteristic value region.

4. The device according to claim 2,
wherein the operation input section is provided to the treatment unit, the treatment unit includes a switch section which is configured to be closed when the operation is input in the operation input section, the detecting section is configured to detect whether the switch section is in an opened state or in a closed state, and the output control section is configured to control the output state of the driving electric power so that the driving electric power is output from the electric power output section only when the detecting section detects that the switch section is in the closed state and detects that the treatment unit is coupled with the vibrator unit.

5. The device according to claim 4,
wherein the switch section is electrically connected to the electronic element through the distal-side electrical path section, and electrically connected to the detecting section through the distal-side electrical path section and the proximal-side electrical path section only when the treatment unit is coupled with the vibrator unit.

6. The device according to claim 5,
wherein the detecting section is configured to detect that the treatment unit is coupled with and the vibrator unit when the electrical characteristic value of the detection electric power is in a first characteristic value region or a second characteristic value region different from the first characteristic value region, and the detecting section is configured to detect that the switch section is in the opened state when the electrical characteristic value of the detection electric power is in the first characteristic value region, and configured to detect that the switch section is in the closed state when the electrical characteristic value of the detection electric power is in the second characteristic value region.

7. The device according to claim 1, further comprising a warning section configured to warn an error state only when the detecting section detects that the treatment unit is not coupled with the vibrator unit.

* * * * *